United States Patent [19]

Miya et al.

[11] Patent Number: 5,215,919
[45] Date of Patent: Jun. 1, 1993

[54] PROCESS FOR PRODUCING OPTICALLY ACTIVE 2-HYDROXYCYCLOALKANECARBOXYLIC ACID ESTERS USING MICROBIALLY DERIVED REDUCTASE

[75] Inventors: Hiroyuki Miya; Mitsuru Kawada, both of Tsukuba; Yoshio Sugiyama, Takasago, all of Japan

[73] Assignee: Takeda Chemical Industries, Ltd., Osaka, Japan

[21] Appl. No.: 836,844

[22] Filed: Feb. 19, 1992

[30] Foreign Application Priority Data

Feb. 25, 1991 [JP] Japan .................. 3-053888
Aug. 5, 1991 [JP] Japan .................. 3-195184

[51] Int. Cl.$^5$ .............................. C07C 29/14
[52] U.S. Cl. ......................... 435/280; 435/832; 435/849; 435/852; 435/873; 435/879; 435/880
[58] Field of Search ............. 435/280, 135, 832, 849, 435/852, 873, 879, 880

[56] References Cited

PUBLICATIONS

Shen G-J, J. Chem. Soc. Chem. Commun: 677-9 (1990).
Seebach et al., Helvetica Chimica Acta., vol. 70 (1987) pp. 1605-1615.
Buisson et al., Tetrahedron Letters, vol. 17, No. 23 pp. 2631-2634 (1986).
Deol et al., Aust. J. Chem. 1976, 29, pp. 2459-2467.

Primary Examiner—David M. Naff
Assistant Examiner—S. Saucier
Attorney, Agent, or Firm—Wenderoth, Lind & Ponack

[57] ABSTRACT

A (1R,2S)-2-hydroxycycloalkanecarboxylic acid ester is efficiently and selectively produced by microbial asymmetric reduction of a 2-oxocycloalkanecarboxylic acid ester with a bacterial strain or its processed material.

14 Claims, No Drawings

PROCESS FOR PRODUCING OPTICALLY ACTIVE 2-HYDROXYCYCLOALKANECARBOXYLIC ACID ESTERS USING MICROBIALLY DERIVED REDUCTASE

FIELD OF THE INVENTION

The present invention relates to a process for producing optically active 2-hydroxycycloalkanecarboxylic acid esters which are useful starting materials for synthesis of good ferroelectric liquid crystal compounds and the like.

When a 2-oxocycloalkanecarboxylic acid ester of the general formula:

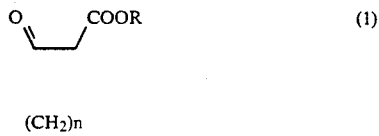

(1)

wherein n is the number of methylene group and R is an ester forming group, is reduced according to an ordinary chemical method, for example, by using $NaBH_4$, the following four stereoisomers are formed due to asymmetric carbon atoms at 1- and 2-positions:

(2)

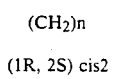

(1R, 2S) cis2

(3)

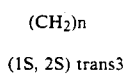

(1S, 2S) trans3

(4)

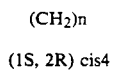

(1S, 2R) cis4

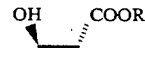

(5)

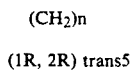

(1R, 2R) trans5 wherein the symbol in the parentheses represents the absolute configuration of the asymmetric carbon atoms at 1- and 2-positions, and n and R are as defined above.

Among these stereoisomers, the present invention relates to a process for the selective production of (1R,2S) cis 2 isomers of the formula (2) by microbial asymmetric reduction. The isomers of formula (2) are highly applicable to synthesis of good ferroelectric liquid crystal compounds as their starting materials.

BACKGROUND OF THE INVENTION

Known processes for producing optically active 2-hydroxycycloalkanecarboxylic acid esters from 2-oxocycloalkanecarboxylic acid esters of the formula (1) by microbial asymmetric reduction include the processes using baker's yeast [Badan S. Deol, et al.:Aust. J. Chem., 29, 2459 (1976); and Dieter Seebach, et al., HELVETICA CHIMICA ACTA, 70, 1605 (1987)] and the process using mold such as *Mucor racemosus* and the like [Didier BUISSON, et al., Tetrahedron Letters, 27, 2631 (1986)]. However, in any of these processes, their reaction efficiency is low as is clear from the fact that 10 to 50 g dry weight of microbial cells is required to reduce 1 g of a substrate. Further, it is difficult to remove a large amount of microbial cells in the recovering step of the reduction product. A yield of the obtained product was very low. Thus, these processes are not industrially advantageous. Furthermore, asymmetric reduction of 2-oxocycloalkanecarboxylates with bacteria has not been known heretofore in the prior art.

OBJECTS OF THE INVENTION

The main object of the present invention is to provide a process for selectively and efficiently producing optically active 2-hydroxycycloalkanecarboxylic acid esters of the formula (2), which are useful starting materials for synthesis of good ferroelectric liquid crystal compounds and the like, from the corresponding oxo esters of the formula (1) by microbial asymmetric reduction.

This object as well as other objects and advantages of the present invention will become apparent to those skilled in the art from the following description.

SUMMARY OF THE INVENTION

The present inventors have found that microbial asymmetric reduction of 2-oxocycloalkanecarboxylic acid esters of the formula:

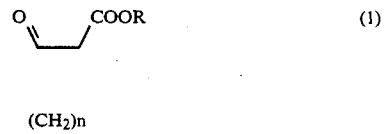

(1)

can be efficiently carried out by using bacteria to form the desired optically active 2-hydroxy isomers.

Namely, according to the present invention, there is provided a process for producing a (1R,2S)-2-hydroxy cycloalkanecarboxylic acid ester of the formula (2) which comprises subjecting a 2-oxocycloalkanecarboxylic ester of the formula (1) to asymmetric reduction with a bacterial strain or its processed material.

DETAILED DESCRIPTION OF THE INVENTION

In the process of the present invention, the number of carbon atoms of the cycloalkane in the 2-oxocycloalkanecarboxylic acid ester of the formula (1) to be used as the starting material is not specifically limited. However, cyclopentane [n=3 in the formula (1)] or cyclohexane [n=4 in the formula (1)] is preferably used. The ester forming group represented by R is not specifically limited. Examples thereof include a lower alkyl group. The lower alkyl group may be a straight or branched chain and may have 1 to 6 carbon atoms. Preferred examples are methyl or ethyl. In particular, the ethyl ester is practically used.

The bacteria used for the asymmetric reduction of the present invention are not specifically limited in so far as they have capability of asymmetric reduction. The bacteria having capability of asymmetric reduction of 2-oxocycloalkanecarboxylic acid ester to (1R, 2S)-2-hydroxycycloalkanecarboxylic acid ester is preferably used. Examples thereof include bacteria belonging to genus Enterobacter, Escherichia, Klebsiella, Proteus, Serratia, Salmonella, Curtobacterium, Cellulomonas and Bacillus. Any strain newly isolated from soil and the like can be used in so far as it is capable of asymmetrically reducing the compound of the formula (1) to produce the compound of the formula (2). Further, the strain may be a mutant obtained by artificial mutagenesis or other bacterial cells integrating a gene fragment necessary for expression of the corresponding reduction activity.

Examples of the bacterial strains used for asymmetric reduction of the 2-oxocycloalkanecarboxylic acid ester of the formula (1) include *Enterobacter aerogenes* IFO 13534, *Enterobacter cloacae* IFO 13535, *Escherichia coli* IFO 3549, *Klebsiella pneumoniae* IFO 3319, *Klebsiella terrigena* ATCC 33257 (IFO 14941, FERM BP-2710), *Proteus vulgaris* IFO 3045, *Salmonella typhimurium* IFO 14194, *Serratia grimesii* IFO 13537, *Curtobacterium citreum* IFO 12677, *Cellulomonas biazotea* IFO 12680, *Bacillus pumilus* IFO 12111 and *Bacillus sphaericus* IFO 12622.

Among these strains, *Klebsiella terrigena* ATCC 33257 is a known strain listed in Catalogue of BACTERIA & BACTERIOPHARGES, Vol. 17 (1989) published by American Type Culture Collection (ATCC), and is readily available from ATCC. This strain has also been deposited at Institute for Fermentation, Osaka (IFO), Japan under the accession number of IFO 14941 since Sep. 14, 1989. Further, it has been deposited at Fermentation Research Institute, Agency of Industrial Science and Technology, Ministry of International Trade and Industry (FRI), Japan according to the Budapest Treaty under the accession number of FERM BP-2710 since Dec. 26, 1989. The other strains are also known strains listed in LIST OF CULTURES, Vol. 8 (1988) published by IFO, and are readily available from IFO.

All of the above-mentioned strains are applicable to the present invention. However, among the strains, some of these strains have excellent specificities to a certain substrate. For example, *Klebsiella pneumoniae* is much suitable for the production of the compound of the formula (2) wherein n is 3, and *Curtobacterium citreum* is much suitable for the production of the compound of the formula (2) wherein n is 4.

For carrying out the process of the present invention, firstly, these bacterial strains are cultivated.

The cultivation of these strains can be carried out continuously or intermittently by means of normal stationary culture, shaking culture, agitating culture or solid culture. Culture media to be used may be those having normal compositions in which the bactria used can be grown. Various carbon sources and nitrogen sources can be used. Examples of the carbon source include sugars (e.g., glucose, sucrose, etc.), sugar alcohol (e.g., glycerol, etc.), various organic acids, fatty acids, alcohols, and the like. Examples of the nitrogen source include an organic nitrogen source such as peptone, yeast extract, meat extract, malt extract, corn steep liquor, soybean meal, urea, etc. and an inorganic nitrogen source such as $(NH_4)_2SO_4$, $NH_4Cl$, $NH_4NO_3$, ammonium phosphate, etc. In addition to these, preferably, essential growth factors and growth promoters such as minerals, amino acids, vitamins and the like which are necessary for growth of the bacterial strains are added to the culture media.

Various alkali solutions such as NaOH aq., KOH aq., etc. or carbonates such as $CaCO_3$, $Na_2CO_3$, etc. can be appropriately added to control pH during the cultivation. Further, it is advantageous to add an anti-foaming agent such as silicone oil, etc. to control bubbling.

Then, the cultivated strain or its processed material is brought into contact with the compound of the formula (1) to carry out the asymmetric reduction.

The bacterial strain to be used for the asymmetric reduction may be the resulting culture as it is or bacterial cells isolated by suitable means such as centrifugation, filtration through various kinds of membranes.

The amount of the bacterial strain or its processed material used for the asymmetric reduction is not limited. An effective amount of the strain or its processed material is generally used. For example, the strain is preferably used in an amount of 0.5 to 8 g as dry cells to 1 g of the substrate, more preferably 0.6 to 7 g as dry cells to 1 g of the substrate. Further, it is also preferred to use the strain in the range of 0.8 to 5 g as dry cells to 1 g of the substrate.

The "processed material" to be used in the present invention includes masticated cells having capability of asymmetric reduction of the compounds of the formula (1) obtained by processing the above bacterial cells or culture by various physicochemical methods. The processed material also includes enzymes contained in these bacterial cells or masticated cells obtained by purifying them according to the methods described hereinafter. Further, the processed material includes the cells and the enzymes immobilized by various methods. The enzymes can be solubilized by subjecting the above-obtained cells to suitable physicochemical treatment. The solubilized enzymes can be purified by further subjecting them one or more conventional enzyme purification operations. The enzyme thus obtained can be immobilized by inclusion in natural or synthetic polymers, or by binding to carriers such as activated charcoal, agarose materials and the like.

When the asymmetric reduction is carried out by bringing the compound of the formula (1) into contact with a culture of the bacterial cells or their processed materials, the compound of the formula (1) is normally used in a concentration of 0.1 to 3% by weight, preferably 0.2 to 2% by weight, more preferably 0.2 to 1.5% by weight. The compound of the formula (1) may be added in one portion or in two or more portions.

Further, when the compound of the formula (1) is reduced by using a culture of bacterial cells or the bacterial cells isolated therefrom, it is desirable to add a carbon source assimilable by the bacterial strain, for example, sugars (e.g., glucose, sucrose, etc.), sugar alcohol (e.g., glycerol, etc.), various organic acids, fatty acids, alcohols, and the like together with the compound of the formula (1) as a hydrogen donor. The concentration of the carbon source is not specifically limited and is normally in the range of 1 to 6% by weight. In order to promote the reaction, minerals or vitamins can also be added.

On the other hand, when the compound of the formula (1) is reduced by using masticated cells or enzymes obtained therefrom, it is necessary to add a coenzyme such as NADPH or NADH as a hydrogen donor together with the compound of the formula (1). In general, in order to increase the turnover number, the asymmetric reduction is preferably coupled with a system for regeneration of the coenzyme because these coenzymes are expensive. For example, in order to regenerate NADPH from NADP, glucose and glucose dehydrogenase can be used in combination. In order to regenerate NADH from NAD, formic acid and formate dehydrogenase can be used in combination.

The reaction temperature is preferably 25° to 50° C. The pH is preferably 5 to 9. For efficient progress of the reduction using culture of bacterial cells or the bacterial cells isolated therefrom, preferably, the reaction mixture is kept under sufficient aerobic conditions.

The reaction is continued until the asymmetric reduction of the compound of the formula (1) is completed. Normally, it takes about 2 to 96 hours.

After the reaction, the optically active 2-hydroxycycloalkanecarboxylic acid ester thus formed can be readily recovered and collected by one or more known purification methods such as extraction, concentration and the like.

The compound of the formula (2) thus obtained by the process of the present invention can be converted into the corresponding 2-alkoxycycloalkanecarboxylic acid by known alkylation of the hydroxy group followed by hydrolysis. Then, the 2-alkoxycycloalkane carboxylic acid is condensed with a side chain component containing no chiral center (or a side chain component optionally containing a chiral center), whereby a good ferroelectric liquid crystal compound having excellent liquid crystal properties can be readily synthesized (see, e.g., EP-A-22862).

As described hereinabove, according to the process of the present invention, (1R,2S)-2-hydroxycycloalkanecarboxylic acid esters such as (1R,2S)-2-hydroxycyclopentane carboxylic acid esters and (1R,2S)-2-hydroxycyclohexane carboxylic acid esters, which are useful starting materials for the production of good ferroelectric liquid crystal compounds and the like can be readily and efficiently produced. In particular, the amount of microbial cells to be used in the process of the present invention is smaller than that in a known process using a yeast or the like and, therefore, the yield of the desired product per unit volume of microbial cells used is much higher than that in a known process. Further, according to the present invention, in comparison with a known process, the product is much readily isolated and purified and losses of the product during recovery step are decreased. Thus, the process of the present invention is industrially advantageous.

The following Examples and Reference Examples further illustrate the present invention in detail but are not to be construed to limit the scope thereof.

EXAMPLE 1

The following reduction was carried out by using ethyl 2-oxocyclopentanecarboxylate as the substrate and the eight strains shown in Table 1.

A bouillon slant culture of each strain was inoculated into a test tube containing a sterilized seed culture medium (pH 7.0, 5 ml) composed of meat extract 1%, polypeptone 1%, NaCl 0.5%, $CaCO_3$ 4% and glucose 2% (separately sterilized), and cultivated on a reciprocal shaker at 30° C. for 24 hours. The seed culture solution (each 0.3 ml portion) was transferred to 200 ml ribbed Erlenmeyer flasks containing a sterilized main culture medium (30 ml) having the same composition as that of the seed culture medium, and cultivated with shaking at 200 rpm at 30° C. After 24 hours from the initiation of the cultivation, the substrate (45 mg) and glucose (800 mg) were added to each flask and the reaction was carried out for 24 hours under the same conditions as those of the cultivation of the main culture. After completion of the reaction, the reaction mixture was extracted twice with the same volume (30 ml) of ethyl acetate. The combined ethyl acetate layer was washed with water, dehydrated and adjust to a predetermined volume. A part of the extract was taken as a sample and the yield of the reduced product and cis/trans ratio were determined by gas chromatography as described hereinafter. On the other hand, a total amount of the remaining extract was concentrated under reduced pressure. The resulting concentrate was dissolved in a small amount of ether and subjected to Kugel distillation to obtain the colorless oily reduction product, ethyl 2-hydroxycyclopentanecarboxylate. The optical purity (enantiomeric excess) was determined by high performance liquid chromatography as described hereinafter.

The results are shown in Table 1. In each strain, high diastereomer selectivity and high enantiomer selectivity are shown.

The amount of cells used to reduce 1 g of the substrate was 6.7 g as dry cells.

The analytical method and conditions used are as follows:

(1) Gas chromatography

Hitachi G-3000 gas chromatography was used. Gas chromatography was carried out by using nonyl alcohol as an internal standard and ethyl (1R,2S)- and (1S,2S)-2-hydroxycyclopentanecarboxylate previously prepared as authentic samples under the following conditions:

column: ULBON HR-20M (0.25 mm × 25 m)
column temperature: 130° C.
carrier gas: He
detection: FID (2) High performance liquid chromatography Waters 600-E high performance liquid chromatography was used. High performance liquid chromatography was carried out by using chemically synthesized four stereoisomers of ethyl 2-hydroxycyclopentanecarboxylate as authentic samples under the following conditions:

column: Daicel OD (4.0 mm × 250 mm)
column temperature: 30° C.
eluent: hexane : 2-propanol = 98:2
flow rate: 1.0 ml/min.
detection: UV 220 nm

TABLE 1

| Strains | Reduction yield (%) | cis/trans ratio | Optical purity (% ee*) |
| --- | --- | --- | --- |
| Enterobacter aerogenes IFO 13534 | 93 | 99/1 | cis 2 = 94 |
| Enterobacter cloacae IFO 13535 | 87 | 98/2 | cis 2 = 94 |
| Klebsiella pneumoniae IFO 3319 | 99 | 99/1 | cis 2 > 99 |
| Klebsiella terrigena ATCC 33257 | 94 | 99/1 | cis 2 > 99 |
| Proteus vulgaris IFO 3045 | 59 | 98/2 | cis 2 = 88 |
| Serratia grimesii | 43 | 97/3 | cis 2 = 96 |

TABLE 1-continued

| Strains | Reduction yield (%) | cis/trans ratio | Optical purity (% ee*) |
| --- | --- | --- | --- |
| IFO 13537 | | | |
| *Bacillus pumilus* IFO 12111 | 48 | 96/4 | cis 2 = 93 |
| *Bacillus sphaericus* IFO 12622 | 55 | 95/5 | cis 2 = 92 |

*ee: enantiomeric excess

EXAMPLE 2

The following reduction was conducted by using ethyl 2-oxocyclohexanecarboxylate as the substrate and the eight strains shown in Table 2.

According to the same manner as that described in Example 1, a bouillon slant culture of each strain was cultivated. After 24 hours from the initiation of the cultivation of the main culture, the substrate (45 mg) and glucose (800 mg) were added to each flask and the reaction was carried out for 24 hours under the same conditions as those of the cultivation of the main culture. After completion of the reaction, the reaction mixture was extracted according to the same manner as that described in Example 1. A part of the extract was taken as a sample and the yield of the reduced product and cis/trans ratio were determined by gas chromatography as described above. The extract was subjected to Kugel distillation to obtain the reduction product, ethyl 2-hydroxycyclohexanecarboxylate. The optical purity (enantiomeric excess) of the reduced product thus obtained was determined by high performance liquid chromatography according to the same manner as that described in Example 1.

The results are shown in Table 2. In each strain, high diastereomer selectivity and high enantiomer selectivity are shown.

The amount of cells used to reduce 1 g of the substrate was 6.7 g as dry cells.

TABLE 2

| Strains | Reduction yield (%) | cis/trans ratio | Optical purity (% ee*) |
| --- | --- | --- | --- |
| *Enterobacter aerogenes* IFO 13534 | >99 | 99/1 | cis 2 = 90 |
| *Escherichia coli* IFO 3549 | >99 | 99/1 | cis 2 > 99 |
| *Klebsiella pneumoniae* IFO 3319 | >99 | 98/2 | cis 2 = 93 |
| *Klebsiella terrigena* ATCC 33257 | 95 | 99/1 | cis 2 = 96 |
| *Salmonella typhimurium* IFO 14194 | 5 | 99/1 | cis 2 > 99 |
| *Serratia grimesii* IFO 13537 | 82 | 89/11 | cis 2 > 99 |
| *Bacillus pumilus* IFO 12111 | 87 | 97/3 | cis 2 = 86 |
| *Bacillus sphaericus* IFO 12622 | 92 | 96/4 | cis 2 = 88 |

*ee: enantiomeric excess

EXAMPLE 3

A bouillon slant culture of *Klebsiella pneumoniae* IFO 3319 was inoculated in a 200 ml Erlenmeyer flask containing a sterilized seed culture medium (pH 7.0, 30 ml) composed of meat extract 1%, polypeptone 1%, NaCl 0.5%, and glycerol 1% (separately sterilized), and cultivated on a rotary shaker at 200 rpm at 30° C. The seed culture solution (20 ml) was transferred to a 5 liter jar fermenter containing a sterilized main culture medium (pH 7.0, 2 liters) composed of meat extract 1%, polypeptone 1%, NaCl 0.5%, an anti-foaming agent 0.05% and glycerol 2% (separately sterilized), and cultivated at 30° C. by aerobic culture with stirring at 800 rpm and at an aeration rate of 0.6 liter/min. When the pH of the culture solution during the cultivation was dropped below 6.0, an aqueous 15% (w/v) sodium hydroxide solution was added to maintain the pH at 6.0. After 24 hours from the initiation of the cultivation, ethyl 2-oxocyclopentanecarboxylate (12 g) was added and the mixture was stirred for 10 minutes. Then, 40% (w/v) glycerol solution (200 ml) was added intermittently at a rate of 8.3 ml/hour. The reaction was carried out under the same conditions as those of the cultivation of the main culture above. At the 24th hour of the reaction, the substrate (12 g) was added again. Then, 20% (w/v) glycerol solution (200 ml) was added intermittently at a rate of 8.3 ml/hour. The reaction was continued for further 24 hours under the same conditions. The pH during the reaction was adjusted according to the same manner as that of the cultivation of the main culture as described above. After completion of the reaction, the reaction mixture (2.41 liters) was extracted once with ethyl acetate (2 liters) and further twice with ethyl acetate (1 liter). The combined ethyl acetate layer was filtered to remove insoluble materials. The filtrate was then washed with water and dehydrated. A part of the extract was taken as a sample and it was analyzed by gas chromatography as described in Example 1. As a result, the remaining substrate was 0.3 g, the yield of the reduction product was 23.3 g (reduction yield: 97%) and cis/trans ratio was 99/1. On the other hand, the ethyl acetate was removed from the remaining extract under reduced pressure to obtain a concentrate (24.0 g). The resulting concentrate was dissolved in a minimum amount of ether and subjected to Kugel distillation to obtain a colorless oily reduction product, ethyl 2-hydroxycyclopentanecarboxylate (23.0 g). The reduction product was separated and determined by high performance liquid chromatography as described in Example 1. As a result, the amounts of cis (2) and trans (3) produced were 22.8 g and 0.2 g, respectively. No cis (4) and trans (5) were detected.

The amount of cells used to reduce 1 g of the substrate was 0.8 g as dry cells.

EXAMPLE 4

A bouillon slant culture of *Klebsiella pneumoniae* IFO 3319 was inoculated in a 200 ml Erlenmeyer flask containing a sterilized culture medium (pH 7.0, 30 ml) composed of meat extract 1%, polypeptone 1%, NaCl 0.5% and glucose 1% (separately sterilized), and cultivated on a rotary shaker at 200 rpm at 30° C. for 24 hours. The culture solution (1 liter) was centrifuged at 10,000×g for 20 minutes to collect cells. The cells were washed with 100 mM phosphate buffer solution (pH 7.0) containing 5 mM 2-mercaptoethanol and 2 μg/ml phenylmethylsulfonyl fluoride. The washed cells were suspended with the above buffer so that the cell concentration became 200 mg wet cell/ml. The cell suspension was sonicated at output of 180 W for 20 minutes by using Kubota insonator 200M to masticate the cells. The resulting mixture was centrifuged at 35,000×g for 20 minutes to remove insoluble materials. Ethyl 2-oxocyclopentanecarboxylate reductase (hereinafter referred to as reductase (1)) was partially purified from the sonic extract through ammonium sulfate fractionation, dialysis and DEAE-5PW ion exchange chromatography. The final preparation (DEAE-5PW active fraction) had 2.6 U/ml of the reductase activity. One unit (U) of the reductase (1) activity is defined as the amount of the enzyme which oxidizes 1 μmol of NADPH per 1 minute in the presence of the above substrate.

The asymmetric reduction of ethyl 2-oxocyclopentanecarboxylate was carried out by using this reductase (1). Namely, 4 ml of the reaction mixture containing the reductase (1) (2U), NADPH (0.8 μmol), ethyl 2-oxocyclopentanecarboxylate (100 μmol, 16 mg), phosphate buffer solution (pH 7.0, 400 μmol), glucose dehydrogenase [manufactured by Sigma, Co., U.S.A.; 2U (wherein 1U is defined as the amount of the enzyme which reduces 1 μmol of NADP+ per 1 minute in the presence of glucose)] and glucose (100 μmol) was incubated at 30° C. with gentle shaking to promote the enzymatic reaction. After 6 hour-incubation, the reaction mixture was extracted according to the same manner as in Example 3. The extract was analyzed by gas chromatography described in Example 1. As a result, the yield of the cis isomer was 15.9 mg (reduction yield >99%), and neither the remaining substrate nor the trans isomer was detected. On the other hand, the extract above was distilled off according to the the same manner as in Example 3 to obtain the reduction product, ethyl 2-hydroxycyclopentane-carboxylate. The resulting reduction product was analyzed by high performance liquid chromatography as described in Example 1. As a result, only the cis 2 isomer was detected and no other isomers were detected.

EXAMPLE 5

According to the same manner as that described in Example 4, *Klebsiella pneumoniae* IFO 3319 was cultivated and, ethyl 2-oxocyclohexanecarboxylate reductase (hereinafter referred to as reductase (2)) was extracted and partially purified from the cells in a similar manner as described in Example 4. The final preparation (DEAE-5PW active fraction) had 5.4 U/ml of the reductase (2) activity. One unit (U) of the reductase (2) activity is defined as the amount of the enzyme which oxidizes 1 μmol of NADPH per 1 minute in the presence of the above substrate.

The asymmetric reduction of ethyl 2-oxocyclohexanecarboxylate was carried out by using this reductase (2). Namely, 4 ml of the reaction mixture containing the reductase (2) (2U), NADPH (0.8 μmol), ethyl 2-oxocyclohexanecarboxylate (100 μmol, 17 mg), phosphate buffer solution (pH 7.0, 400 μmol), glucose dehydrogenase (the same enzyme as that used in Example 4; 2U) and glucose (100,μmol) was incubated at 30° C. with gentle shaking to promote the reaction. After 4 hour-incubation, the reaction mixture was extracted according to the same manner as in Example 3. The extract was analyzed by gas chromatography described in Example 1. As a result, the yield of the cis isomer was 17.0 mg (reduction yield >99%), and neither the remaining substrate nor the trans isomer was detected. On the other hand, the extract above was distilled off according to the the same manner as in Example 3 to obtain the reduction product, ethyl 2-hydroxycyclohexanecarboxylate. The resulting reduction product was analyzed by high performance liquid chromatography described in Example 1. As a result, only the cis 2 isomer was detected and no other isomers were detected.

EXAMPLE 6

Ethyl 2-oxocyclohexanecarboxylate was reduced by two bacterial strains listed in Table 3, in a similar manner as described in Example 1 except that the amount of the substrate added was 120 mg per flask. After the completion of the reaction, according to the same manner as that described in Example 1, the reduction product was extracted from the reaction mixture. The yield of the reduction product, ethyl 2-hydroxycyclohexanecarboxylate, the cis/trans ratio and the optical purity (enantiomeric excess) were determined.

The results are shown in Table 3. In both strains used, high diastereomer selectivity and high enantiomer selectivity are shown.

The amount of cells used to reduce 1 g of the substrate was 2.5 g as dry cells.

TABLE 3

| Strains | Reduction yield (%) | cis/trans ratio | Optical purity* (% ee) |
|---|---|---|---|
| Curtobacterium citreum IFO 12677 | 99 | 99/1 | cis 2 = 98 |
| Cellulomonas biazotea IFO 12680 | 99 | 98/2 | cis 2 = 98 |

*ee: enantiomeric excess

EXAMPLE 7

A bouillon slant culture of *Curtobacterium citreum* IFO 12677 was inoculated in two 2 liter Sakaguchi flasks, each containing a sterilized seed culture medium (pH 7.0, 500 ml) composed of meat extract 1%, polypeptone 1%, NaCl 0.5%, and glucose 1% (separately sterilized), and cultivated on a reciprocal shaker at 120 spm at 28° C. for 24 hours. The seed culture solution (1 liter) was transferred to a 200 liter fermenter containing a sterilized main culture medium (pH 7.0, 120 liters) composed of meat extract 1%, polypeptone 1%, NaCl 0.5%, an anti-foaming agent 0.04% and glucose 2% (separately sterilized). Submerged culture was then performed under the following conditions; internal pressure, 1.0 kg/cm$^2$; aeration, 40 liters/min; agitation, 150 rpm; temperature, 30° C. When the pH of the culture solution was dropped below 6.0 during the cultivation, an aqueous 30% (w/v) sodium hydroxide solution was added to maintain the pH at 6.0. Glucose was completely consumed after 24 hours from the initiation of the cultivation, and the cell yield reached to 10 g dry weight/liter. At this point of time, 40% (w/v) glucose solution (6 liters) followed by ethyl 2-oxocyclohexane carboxylate (350 g) was added and the reaction was carried out under the same conditions as those of the cultivation of the main culture above. After the reaction for 24 hours, 40% (w/v) glucose solution (6 liters) and the same substrate (350 g) were added again and the reaction was carried out for additional 24 hours under the same conditions. During the reaction the pH was adjusted according to the same manner as that of the cultivation of the main culture as described above.

After completion of the reaction, 1N HCl (350 ml) was added to the reaction mixture (132 liters) thus obtained to adjust the pH to 5.5. To the mixture was then added successively with stirring 0.5% (w/v) Press Aid ® 101 (manufactured by Kurita Kogyo, Japan) solution (6 liters), Radiolite ® #500 (manufactured by Showa kagaku Kogyo, Japan, 1.2 kg) and 0.2% (w/v) Press Aid ® 201 (manufactured by Kurita Kogyo, Japan) solution (0.6 liters). The mixture was filtered under pressure by using a filter press (about 1.76 m² of filtration area) pre-coated with Radiolite ® #500. The filtration proceeded rapidly and clear filtrate (130 liters) was obtained after about 30 minutes. Water (10 liters) was fed to the filter press to wash the cake. The washing obtained was combined with the above filtrate. The combined liquid (140 liters) was extracted twice with ethyl acetate (120 liters) to obtain an ethyl acetate layer (240 liters). This extract was washed twice with water (10 liters) and then concentrated successively to 12 liters. The concentrated mixture was subjected to distillation under reduced pressure to obtain 568 g of the main fraction (b.p.: 95°–97° C. (2 mmHg)). The reduction product, ethyl 2-hydroxycyclohexanecarboxylate contained in this main fraction was determined by high performance liquid chromatography as described in Example 1 to obtain cis 2 (558 g), cis 4 (2 g), trans 3 (3 g) and trans 5 (4 g). Namely, the total yield of the reduction product was 81%, the cis/trans ratio was 99/1 and the ee was cis 2=99.2%. The amount of cells used to reduce the substrate (1 g) was 1.7 (g as dry cells).

REFERENCE EXAMPLE 1

Synthesis of 4'-octyloxy-4-biphenylyl cis-(1R,2S)-2-methoxycyclopentane-1-carboxylate i) Synthesis of cis-(1R,2S)-2-methoxycyclopentane-1-carboxylic acid Ethyl cis-(1R,2S)-2-methoxycyclopentane-1-carboxylate was obtained by subjecting the ethyl cis-(1R,2S)-2-hydroxycyclopentane-1-carboxylate obtained in Example 3 to the following conventional methyl-etherification of hydroxyl group [Method A: CH₃I (methyl iodide)/ Ag₂O (silver oxide)/ CH₃CN (acetonitrile) or Method B: CH₃I (methyl iodide)/ NaH (sodium hydride)/ DMF (dimethylformamide)].

Method A: Ethyl cis-(1R,2S)-2-hydroxycyclopentane-1-carboxylate (5.65 g) was dissolved in acetonitrile (60 ml). Methyl iodide (60 ml) and silver oxide (12.5 g) were added thereto with stirring at room temperature. The reaction mixture was stirred at 50° C. for 10 hours and then filtered to remove insoluble materials. The filtrate was concentrated under reduced pressure and the resulting residue was subjected to Kugel distillation (external temperature: 150° C., 17.5mmHg) to obtain ethyl cis-(1R,2S)-2-methoxycyclopentane-1-carboxylate (yield: 6.19 g) in a quantitative yield as a colorless oil.

Method B: Ethyl cis-(1R,2S)-2-hydroxycyclopentane-1-carboxylate (23.72 g) was dissolved in dimethylformamide (240 ml). Methyl iodide (213 g) was added thereto, and then 60% oily sodium hydride (9.0 g) was added by portions with stirring at 0° C. to 5° C. After the completion of the addition, the mixture was stirred for one hour at 0° C. to 5° C. Then, ice water containing dil. hydrochloric acid and ethyl acetate were added with caution to the reaction mixture. The ethyl acetate layer was separated and collected and the aqueous layer was extracted with ethyl acetate. The combined ethyl acetate layer was dried over sodium sulfate and concentrated under reduced pressure. The residue was distilled under reduced pressure to obtain ethyl cis-(1R,2S)-2-methoxycyclopentane-1-carboxylate (23.2 g, yield: 89.8 %) as a colorless oil.

Ethyl cis-(1R,2S)-2-methoxycyclopentane-1-carboxylate (6.19 g) thus obtained was dissolved in dioxane (60 ml), water (60 ml) and conc. hydrochloric acid (60 ml) and the mixture was stirred at 80° C. for 3 hours.

The reaction mixture was concentrated and the residue was distilled under reduced pressure to obtain cis-(1R,2S)-2-methoxycyclopentane-1-carboxylic acid (4.74 g, yield: 91.5%) a as colorless oil.

¹H-NMR and IR spectra of this compound are as follows:

¹H-NMR (90 MHz, CDCl₃) δ: 1.4–2.25 (6H, m, CH₂), 2.6–3.05 (1H, m, >CHCOO), 3.35 (3H, s, OCH₃), 3.85–4.15 (1H, m, >CHOCH₃), 7.7–8.6 (1H, broad s, CO₂H)

IR $\nu_{max}^{neat}$: 2700–2400, 1710 cm⁻¹ ii) Esterification

To a solution of 4'-octyloxy-4-biphenol (0.68 g) and pyridine (0.6 ml) in dry tetrahydrofuran (10 ml) was added with stirring at room temperature a solution of the acid chloride (382.5 mg, IR $\nu_{max}^{neat}$: 1800 cm⁻¹)

of cis-(1R,2S)-2-methoxycyclopentane-1-carboxylic acid, which was obtained by reacting the acid (472.5 mg) obtained in i) with oxalyl chloride, in dry toluene (5.0 ml). The insoluble materials were removed by filtration and the filtrate was concentrated under reduced pressure. The residue was subjected to column chromatography using silica gel (150 g) and carbon tetrachloride-ether (10 : 1). The desired fraction gave the title compound (0.44 g) as waxy crystals.

¹H-NMR and IR spectra of this compound are as follows:

¹H-NMR (90 MHz, CDCl₃) δ: 0.89 (3H, t, J=6Hz, —CH₂CH₃), 1.0–2.5 (18H, m, CH₂), 2.9–3.4 (1H, m, >CH—COO), 3.39 (3H, s, OCH₃), 3.99 (2H, t, J=6Hz, OCH₃), 3.9–4.25 (1H, m, >CH-OCH₃), 6.75–7.6 (8H, m, aromatic ring H)

IR $\nu_{max}^{neat}$: 1755, 1500, 1245, 1210, 1165 cm⁻¹

REFERENCE EXAMPLE 2

Synthesis of 4'-(4-octyloxyphenyl)-4-biphenylyl cis-(1R,2S)-2-methoxycyclohexane-1-carboxylate i) Synthesis of cis-(1R,2S)-2-methoxycyclohexane-1-carboxylic acid Ethyl cis-(1R,2S)-2-methoxycyclohexane-1-carboxylate was obtained by subjecting the ethyl cis-(1R,2S)-2-hydroxycyclohexane-1-carboxylate obtained in Example 2 to the following conventional methyletherification of the hydroxyl group [Method A: CH₃I (methyl iodide)/ Ag₂O (silver oxide)/CH₃CN (acetonitrile) or Method B: CH₃I (methyl iodide)/NaH (sodium hydride)/DMF (dimethylformamide)].

Method A: Ethyl cis-(1R,2S)-2-hydroxycyclohexane-1-carboxylate (5.17 g) was dissolved in acetonitrile (52 ml). Methyl iodide (52 g) followed by silver oxide (10.4 g) was added by portions with stirring at room temperature. The reaction mixture was stirred at 50° C. for one day and then insoluble materials were removed by filtration. The filtrate was concentrated under reduced pressure and the resulting residue was subjected to Kugel distillation to obtain ethyl cis-(1R,2S)-2-methoxycyclohexane-1-carboxylate (4.8 g, yield: 86%) as a colorless oil.

Method B: Ethyl cis-(1R,2S)-2-hydroxycyclohexane-1-carboxylate (20.6 g) was dissolved in dimethylformamide (200 ml). Methyl iodide (170 g) followed by 60% oily sodium hydride (7.2 g) was added by portions with stirring at 0° C. to 5° C. After the completion of the addition, the mixture was stirred for an hour at 0° C. to 5° C. Then, ice water containing dil. hydrochloric acid and ethyl acetate were added with caution to the reaction mixture. The ethyl acetate layer was separated and collected and further the aqueous layer was extracted with ethyl acetate. The combined ethyl acetate layer was dried over sodium sulfate and concentrated under reduced pressure. The residue was distilled under reduced pressure to obtain ethyl cis-(1R,2S)-2-methoxycyclohexane-1-carboxylate (20.0 g, yield: 89.5%) as a colorless oil.

Ethyl cis-(1R,2S)-2-methoxycyclohexane-1-carboxylate (20.0 g) was dissolved in dioxane (400 ml) and 4N hydrochloric acid (140 ml). The mixture was stirred under reflux overnight. The reaction mixture was concentrated to obtain a crude sample of cis-(1R,2S)-2-methoxycyclohexane-1-carboxylic acid (15.1 g, crude yield: 86.9%).

ii) Esterification

To a solution of 4-octyloxyphenyl ester (1.05 g) of 4'-hydroxy-4-biphenylcarboxylic acid and pyridine (0.6 g) in dry tetrahydrofuran (10 ml) was added with stirring at room temperature the acid chloride of cis-(1R,2S)-2-methoxy-cyclohexane-1-carboxylic acid (0.5 g, IR $\nu_{max}^{neat}$: 1800 cm$^{-1}$), which was obtained by reacting the acid (4.0 g) obtained in i) with oxalyl chloride. The reaction was carried out overnight and then the reaction mixture was concentrated under reduced pressure. The residue was subjected to column chromatography using silica gel (150 g) and carbon tetrachloride-ether (30:1) and recrystallized from ethanol to obtain the title compound (0.3 g).

$^1$H-NMR and IR spectra of this compound are as follows:

$^1$H-NMR (90 MHz, CDCl$_3$) δ: 0.89 (3H, t), 1.1–2.0 (20H, m), 2.6–2.9 (1H, m), 3.40 (3H, s), 3.9–4.1 (3H, m), 6.8–8.3 (12H, m)

IR $\nu_{max}^{KBr}$: 2800–3000, 1740, 1605 cm$^{-1}$

What is claimed is:

1. A process for producing a (1R,2S)-2-hydroxycycloalkanecarboxylic acid ester which comprises subjecting a 2-oxocycloalkanecarboxylic acid ester to asymmetric reduction with a bacterial strain belonging to *Enterobacter aerogenes, Enterobacter cloacae, Escherichia coli, Klebsiella pneumoniae, Klebsiella terrigena, Proteus vulgaris, Salmonella typhimurium, Serratia grimesii, Curtobacterium citreum, Cellulomonas biazotea, Bacillus pumilus* or *Bacillus sphaericus,* or its processed material containing reductase and recovering said ester.

2. A process according to claim 1, wherein the bacterial strain is selected from the group consisting of *Enterobacter aerogenes* IFO 13534, *Enterobacter cloacae* IFO 13535, *Escherichia coli* IFO 3549, *Klebsiella pneumoniae* IFO 3319, *Klebsiella terrigena* ATCC 33257 (IFO 14941, FERM BP-2710), *Proteus vulgaris* IFO 3045, *Salmonella typhimurium* IFO 14194, *Serratia grimesii* IFO 13537, *Curtobacterium citreum* IFO 12677, *Cellulomonas biazotea* IFO 12680, *Bacillus pumilus* IFO 12111 and *Bacillus sphaericus* IFO 12622.

3. A process according to claim 1, wherein the (1R,2S)-2-hydroxycycloalkanecarboxylic acid ester is (1R,2S)-2-hydroxycyclopentanecarboxylic acid ester.

4. A process according to claim 3, wherein the bacterial strain is that of *Klebsiella pneumoniae.*

5. A process according to claim 1, wherein the (1R,2S)-2-hydroxycycloalkanecarboxylic acid ester is (1R,2S)-2-hydroxycyclohexanecarboxylic acid ester.

6. A process according to claim 5, wherein the bacterial strain is that of *Curtobacterium citreum.*

7. A process according to claim 1, wherein the processed material is masticated bacterial cells.

8. A process according to claim 1, wherein the processed material is a reductase contained in the bacterial strain.

9. A process according to claim 1, wherein the 2-oxocycloalkanecarboxylic acid ester is used in a concentration of 0.1 to 3% by weight.

10. A process according to claim 9, wherein the 2-oxocycloalkanecarboxylic acid ester is used in a concentration of 0.2 to 2% by weight.

11. A process according to claim 10, wherein the 2-oxocycloalkanecarboxylic acid ester is used in a concentration of 0.2 to 1.5% by weight.

12. A process according to claim 1, wherein asymmetric reduction is carried out at 25° to 50° C.

13. A process according to claim 1, wherein asymmetric reduction is carried out at pH 5 to 9.

14. A process according to claim 1, wherein asymmetric reduction is carried out for 2 to 96 hours.

* * * * *